United States Patent [19]

Ersek et al.

[11] Patent Number: 4,955,909
[45] Date of Patent: Sep. 11, 1990

[54] TEXTURED SILICONE IMPLANT PROSTHESIS

[75] Inventors: Robert A. Ersek, Austin, Tex.; Arthur A. Beisang, Roseville, Minn.; Arthur A. Beisang, III, Des Moines, Iowa

[73] Assignee: Bioplasty, Inc., St. Paul, Minn.

[21] Appl. No.: 304,764

[22] Filed: Jan. 31, 1989

[51] Int. Cl.$^5$ ............................ A61F 2/02; A61F 2/12
[52] U.S. Cl. ........................................... 623/11; 623/8
[58] Field of Search ............................ 623/7, 8, 11, 66

[56] References Cited

U.S. PATENT DOCUMENTS 4,531,244  7/1989  Hamas ..................................... 623/8
4,820,303  4/1989  Brauman ................................. 623/8
4,889,744  12/1989  Quaid ................................. 623/8 X

OTHER PUBLICATIONS

McGhan, Biocel Textured Mammary Implant, 10/87.
Picha et al., Ion–Beam Microtexturing of Biomaterials, 4/84, pp. 39–42.

Primary Examiner—Alan W. Cannon
Assistant Examiner—N. Paul
Attorney, Agent, or Firm—Haugen and Nikolai

[57] ABSTRACT

Capsular contracture causing firmness of soft silicone implants is a serious problem that may result from several causative factors that have as their final pathway, the development of increased scar tissue. The present invention has altered the formation of this scar encapsulation of silicone implants by texturing the silicone surface in order to gain fibroblast ingrowth into the interstices and thus prevent micromotion at the host prosthesis interface. It has been found that this produces a thinner fibrous capsule. Previously published work pertaining to animals and man has shown that similar texturing of tetrafluoroethylene (Teflon) and other substances achieves these goals. In accordance with work leading up to the present invention, textured silicone samples have been implanted in the subcutaneous layer of rabbits, the capsule formation and the host-prosthesis interface studied histologically. A difference between the smooth surface and the textured surface could be measured wherein the textured surface had a thinner capsule without contracture and the smooth surface had a thicker capsule with contraction.

5 Claims, 2 Drawing Sheets

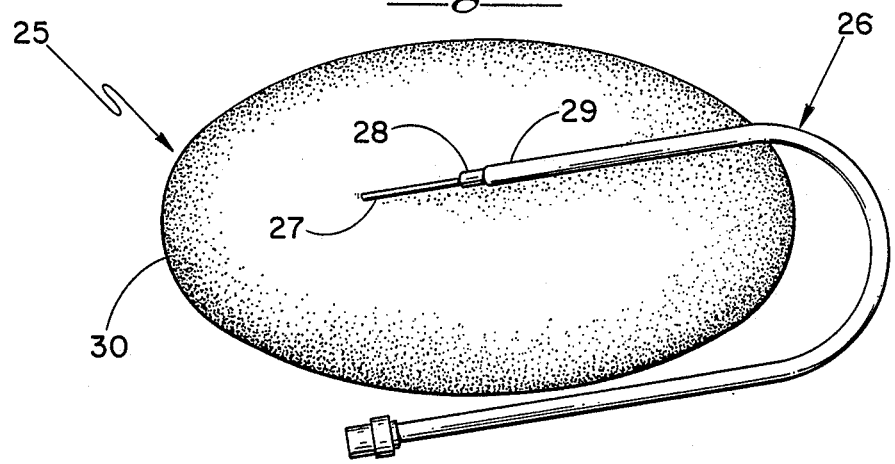
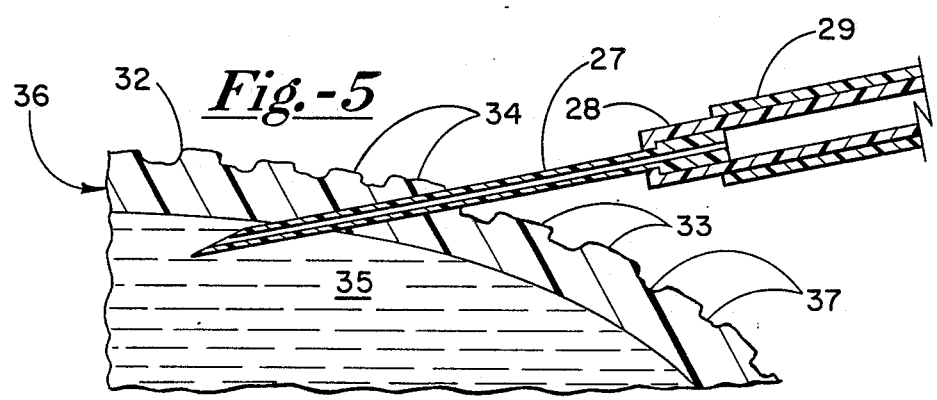

TEXTURED SILICONE IMPLANT PROSTHESIS

BACKGROUND OF THE INVENTION

Capsular contracture around breast prostheses is the principal cause for dissatisfaction in breast augmentation. All breast prosthesis are soft, pliable and adjust to a pleasing shape when first installed; but the body's response to the presence of the implant may later cause contracture. Alterations must be made in the prosthesis or the body's response to affect the capsule formation in the future. McGrath and Burkhardt, "The Safety and Efficacy of Breast Implants for Augmentation Mammoplasty", *Plastic Reconstr. Surg.*, 74:550–560 (1984), have published an extensive review of certain developments and also difficulties in attempting to control scar tissue formation around soft silicone implants. In some 251 studies, it was shown that up to 74% develop contractures, but only one-half are bilateral. The disease is capsular contracture (the problem being believed to be created by the contractile myofibroblast) and the mechanism has been studied and described. The contributing factors of infection, inflammation, hematoma formation and unknown factors all lead to increased scar formation. Attempts to alter this basic response have been diverse and evolving over many years. These studies were designed to alter the surface morphology of the prosthesis so as to influence the capsule's characteristics for softer breasts.

One of the most fertile frontiers of plastic surgery is the host prosthesis interface. The development of dependable prosthetic devices is generally directed or related to the creation of a non-space between the host and the prosthesis. The earliest advances in prosthetic implantation were made when a variety of substances were discovered and developed that were relatively inert so they could remain in tissue without disturbing the physiology of the host. All implants elicit a foreign body reaction, and all implants are subject to an initial inflammatory phase where the host attempts to either eliminate or encapsulate the prosthesis. Control of this inflammation and encapsulation may be achieved by altering the host-prosthesis interface. The inflammatory phase of wound healing lasts for about one week; the phase of fibrosis or collagen deposition begins and increases for a few weeks. Once encapsulation is complete, collagen deposition and degradation approach equilibrium and the scar matures within 30–60 days if the host is in good health and no outside forces influence the host-prosthesis interface. In the case of structurally hard substances such as ceramics, stainless steel, and other inert metals and hard plastics, the amount and degree of encapsulation does not affect their function, but only their fixation. The stability of bone prostheses is greatly enhanced if tissue, particularly bone tissue ingrowth can be induced. This has been accomplished in the past by sintering or texturing the surface or attaching porous substance that would allow some tissue ingrowth. Where silicone rubber blocks and pre-formed prosthetics, which in the nose, and other sites, were function-dependent on form, encapsulation proceeded in a similar way and was not a problem. Fibroblasts actually migrate along a substrata (plastic) and lay down collagen as a mirror image of the substrate through contact guidance. Fibrosis and increased collagen production cease when fibroblasts contact other fibroblasts, normally termed contact inhibition.

The development, however, of soft, pliable prosthetic implants for breast enlargement and other body contour problems has been successful to the extent that the foreign body reaction could be minimized, and initially, the host prosthesis interface was made as smooth as possible. It was hoped that this smooth surface would elicit a minimal foreign body reaction, and since silicone rubber is a relatively inert substance, it would be ignored by the body. Indeed, this was found to be true in most cases. This smooth surface, however, prevents any attachment of the scar capsule to the prosthesis so that any movement of the host creates a shearing effect if any microscopic surface irregularity, such as the edge of a fill patch or a mold seam or a fold flaw corner. However, if inflammation was increased by local infection or inadvertent hematoma formed, the amount of fibrosis was greatly increased. If after a long quiescent period of pliability and stability, the prosthesis was subject to trauma, so that subcapsular bleeding ensued, or infection in a nearby area unrelated to the surgery caused increased inflammation and scar tissue, an encapsulation response was often elicited even though many months or years of soft quiescent implantation had preceded.

As early as 1969 successes were achieved in altering the surface characteristics of tetrafluoroethylene (Teflon-trademark of the du Pont Company of Wilmington, Del.) implants by texturing, this allowing for an intimate, flexible host-prosthesis interface to be developed with a thinner encapsulation with random axis collagen fibrils and a firm mechanical bond between the inert tetrafluoroethylene (Teflon) and the host, including both animals and humans. In these experiments and clinical applications, a waterproof, germ-proof seal was created between the host and inert tetrafluoroethylene (Teflon) prosthesis that was a thin stable scar, when compared to the chronic inflammatory, thick scar pseudo-bursa around the smooth shunts. Other controlled studies have shown inert textured tetrafluoroethylene (Teflon) in rabbits creates a thinner capsule.

In subsequent work with semi-synthetic implants, such as human umbilical cords and vascular conduits, it was found that the outer surface, being textured by a mechanical process to create a net-like textured surface, allowed for the intimate intertwining of the capsule collagen and the interstices of the texturing, so that an effective host prosthesis interface would be developed that would prevent perigraft pseudoaneurysms, even in the face of repeated punctures, as in dialysis access. The previous work with the semi-synthetic glutaraldehyde cross-linked chondroplast in monkeys showed that the classic foreign body reaction and encapsulation resulted in a scalloping or texturing of the surface of this otherwise smooth substance. This texturing was shown to create an effective host prosthesis interface with a minimal encapsulation response and a thinner capsule with multi-planar random axis orientation of the fibers. When compared with silicone rubber blocks in the same animal, in the same site, at the same time, it was noted that the textured chondroplast elicited a thinner capsule and on electron-microscopy, this thin capsule had a cellular surface with few free collagen fibrils. The seemingly smooth silicone rubber, however, elicited a four times thicker mono-planar aligned capsule with a surface of free fibrils of collagen.

Taylor and Gibbons ("Effective Surface Texture on the Soft Tissue Response to Polymer Implants", *Journal of Biomedical Materials Research*, 17:205–277 (1984)), have shown that just altering the surface texture of inert tetrafluoroethylene (Teflon) alters the host response as a result of that texture. Specifically, this texturing of tetrafluoroethylene (Teflon) in their studies resulted in a thinner capsule with less cellular activity than a perfectly smooth implant of the same material in the same animal at the same time. Their work implies that texturing prevents the host prosthesis interface action (micromotion) with its repeated mechanical trauma to the surface cell. Texturing the surface of a prosthesis to prevent chest wall adhesion to the myocardium and following cardiac surgery has shown that the textured surface aids the host in isolating and destroying infection, whereas smooth, seemingly serosal surfaces allow for the rapid spread of infection.

These earlier experiments and observations have led to the improvements of the present invention, including development of surface textured implants to allow for the mechanical ingrowth of host fibrous tissue to produce a mechanical bond of the host prosthesis interface and prevent micromotion. It appears that the texturing of the surface in accordance with the present invention allows for the fibroblast to grow into and around the interstices of the surface and thus, at least on several planes, touch another fibroblast. The capsule of the textured surface has collagen fibers that are arranged in a random axis pattern that generally follows the random directions of the textured surface, and this way, the contractile forces of the contractile myofibroblasts to some extent cancel each other out. Recent papers of others support this concept.

The human fibroblast is described as a pleomorphic cell of mesenchymal origin. This cell is approximately 20 to 100 microns in size. Therefore, in order to have any effect on the configuration of the capsule produced by these fibroblasts, it has been determined that indentations must be at least in the 20 to 100 micron range. Texturing with hills and valleys greater than 2 mm. might alter the surface so drastically as to be seen or felt through the skin of a thin-skinned individual. By impacting the surface of silicone implants prior to vulcanization, it is possible to create surfaces that approximate the desired irregularities as hills and valleys in a net-like three-dimensional grid. It is possible to create a reverse image of an imaginary fibroblast colony by creating "designer molecules" to create a friendly environment for the host cells. This method provides a variety of precise hills and valleys wherein few of the indentations communicate with each other, but the hills have very irregular surfaces. The use of open-cell foam may allow some tissue ingrowth on the surface, but it also produces unfathomable caves and indentations where bacteria may thrive. Contact inhibition by these random axis fibroblasts may result in a thinner capsule formation. The textured accordion-pleat like surfaces may allow for some spring-like expansion of the surface. This is generally the random direction of collagen found in skin, which is flexible. The smooth surfaced prosthesis, however, elicits a fibrous reaction wherein all of the collagen fibrils are aligned, in a cumulative manner, in one spherical plane. This way, the contractile forces of the contractile myofibroblasts, if stimulated, will be parallel and tangential to the surface of the prosthesis, since it is a continuous surface. This is the exact configuration of collagen in tendons, which does not yield. All of these additive forces are in parallel alignment.

Attempts by others to use polyurethane foam and polyethylene terephthalate (Dacron-trademark of the du Pont Company of Wilmington, Del.) fabric and other substances has led to some earlier reports of improved host prosthesis interface reaction because of these mechanical factors. However, since the polyurethane foam biodegrades into questionable substances and since the disappearance of the urethane leaves a partially smooth silicone prosthesis after some period of time, its benefits appear to be temporary at best. In addition, the late infection rate of this urethane foam may be related to the chronic inflammatory response that may cause a pink rash and softer prosthesis. By texturing silicone rubber in a predetermined pattern, we may be able to alter the host response to wound healing now, so that tissue ingrowth may produce the host prosthesis interface that would be more stable, more compatible, thinner and remain soft longer, and decrease capsular contracture in the future.

SUMMARY OF THE INVENTION

In accordance with the present invention, silicone rubber film was prepared in accordance with the usual multiple dipping method employed commercially by manufacturers of conventional silicone breast prostheses. One surface of the film, following its preparation, was textured by selecting specific molecules whose shape and size produce three-dimensional projections of from 20 to 500 microns in size. Prior to vulcanization of the silicone, these molecules were thrust onto one surface with sufficient impact to alter the surface morphology. A pattern was designed with randomization including large pillars and indentations with the hills and valleys having further indentations on the surfaces. The smaller indentations were in the 20 to 100 micron range, and the larger dimensions were from approximately ten to twenty times that size. Accordingly, an irregular surface was formed with pore sizes of between about 20 and 800 microns arranged in a net-like pattern so as to form a multi-planar random axis orientation of the collagen fibers. This silicone rubber film was utilized as the outer skin of a gelfilled member forming the three-dimensional soft, pliable prosthesis of the present invention.

Therefore, it is a primary object of the present invention to provide an improved soft, pliable prosthesis means for implantation in humans, particularly as a breast implant, which has its surface treated so as to become textured with randomly arranged large pillars and indentations, and wherein a net-like pattern is formed with random axis orientation for collagen fibers.

It is a further object of the present invention to provide an improved soft, pliable prosthesis utilizing a silicone rubber film enveloping a gel, and wherein the outer surface of the silicone rubber film is textured to produce three-dimensional projections of from 20 to 500 microns in size.

Other and further objects of the present invention will become apparent to those skilled in the art upon a study of the following specification, appended claims, and accompanying drawings.

IN THE DRAWINGS

FIG. 4 is a view similar to FIG. 1, but illustrating an embodiment of the invention wherein gel may be introduced into the prosthesis either prior to or following implantation; and FIG. 5 is a detail sectional view showing the manner in which a quantity of gel may be added to the inner core of the prosthesis.

DESCRIPTION OF THE PREFERRED EMBODIMENT

Figure 1:
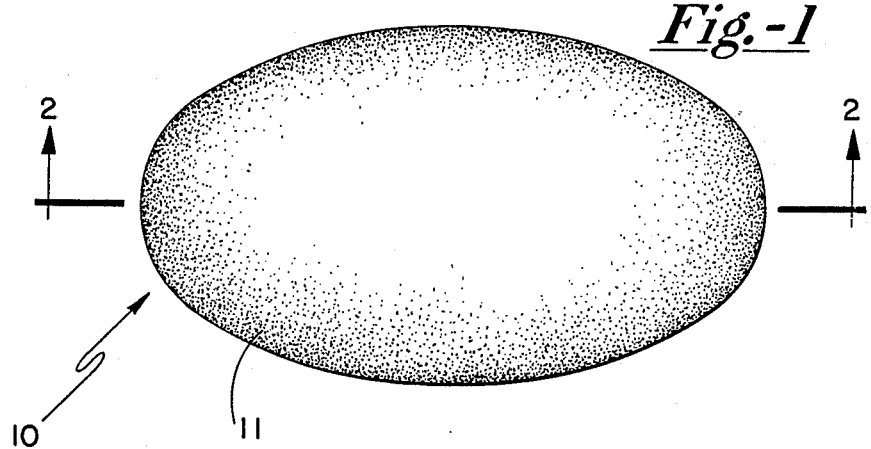
FIG. 1 is a plan view of a soft, pliable breast prosthesis prepared in accordance with the present invention.

In order to provide a description of the preparation of a soft, pliable prosthesis device in accordance with the present invention, the following specific example is given.

EXAMPLE I (A) Methods and Materials

Silicone rubber film was made by the usual multiple dipping method employed by the manufacturers of silicone breast prostheses. One surface of the silicone film was textured by selecting specific molecules whose shape and size produce three-dimensional projections of 20 to 500 microns. Prior to vulcanization, these molecules were thrust onto one surface with sufficient impact to alter the surface morphology. We designed a pattern with some randomization with large pillars and indentations with the hills and valleys having further indentations on the surfaces, so that the smaller indentations were in the 20 to 100 micron range, and the larger dimensions were ten to twenty times that size. This produced the irregular surface characteristics with pore size of 20 to 800 microns in a net-like pattern that will form a multi-planar random axis orientation of the collagen fibers.

(B) Results

In animal testing, all of the implants had some encapsulation and no known infection. The encapsulation was minimal on both the smooth and the textured surfaces in the short-term experiments. In the last series of 131 days, a substantial difference could be seen wherein the textured surface could be seen to have multi-planar distributions of its collagen fibrils and the smooth surface is shown to have a mono-planar orientation of these collagen fibrils. Further, the ratio of the capsule wall thickness was approximately one to four, being thinner on the textured side of the same capsule.

(C) Discussion

Early work with constant level hills and valleys did not produce a host prosthesis interface that altered the capsule. When all of the indentations were in the 100 micron range, with the pillars 100 microns across, though some fibroblasts appeared to enter into these valleys and a slight waviness of the surface collagen could be seen a few cell distances above the surface, the reaction was that of a foreign body reaction with encapsulation and the slight variations in the host prosthesis interface did not affect the orientation of the collagen fibrils in a generally mono-planar direction.

While the precise mechanism is not fully understood at this time, it may be "contact inhibition" which is responsible for the thinner capsule formation of the textured surface, because the fibroblasts touch each other in several planes. Since "contact guidance" directs the fibroblast into the crevices and indentations of the substrate surface, the advancing edge of the fibroblast will contact the other fibroblasts in many planes, and on several surfaces. Whereas, when in contact with the surface of a smooth substrate, the entire portion of the cell that is in contact with the silicone rubber prevents contact with other cells, except at their very periphery. Further, this texturing prevents micromotion on the host prosthesis interface so that the fibroblasts are not mechanically stimulated or irritated to repeatedly produce collagen in response to this host-prosthesis shearing motion. Previous work has led to the conclusion that a textured surface promotes tissue ingrowth. This has been shown to be true for a variety of prosthesis surfaces and substances. In orthopedic applications, the desire is to minimize scar tissue formation and maximize new bone formation with the interstices of the surface texturing of the prosthesis. Experiments have shown that the optimum surface irregularity size is between 80 and 500 microns. Soft prostheses have only recently attracted the attention of having the surface altered and this has been done in a random fashion by the application of polyurethane foam to a standard silicone gel prosthesis. This has resulted in a high infection rate, a high rate of foam separation from the prosthesis, unexplained sub-sponge hematoma formation, and great difficulty in inserting these devices. However, early reports dealing with the devices of the present invention suggest a substantial decrease in the formation of firm capsules. The present inventors have previously reported on the surface alteration of a variety of substances to allow for a predictable degree of host tissue ingrowth and the creation of a stable, compatible host prosthesis interface.

(D) Structure

Figure 2:
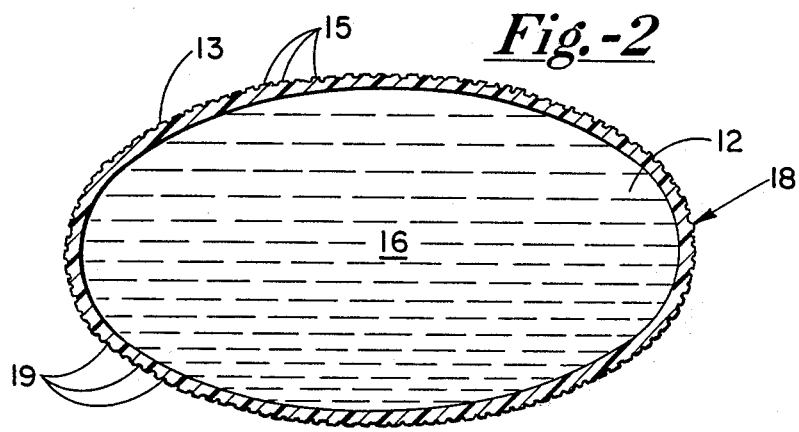
FIG. 2 is a vertical sectional view taken along the line and in the direction of the arrows 2—2 of FIG. 1.
Figure 3:
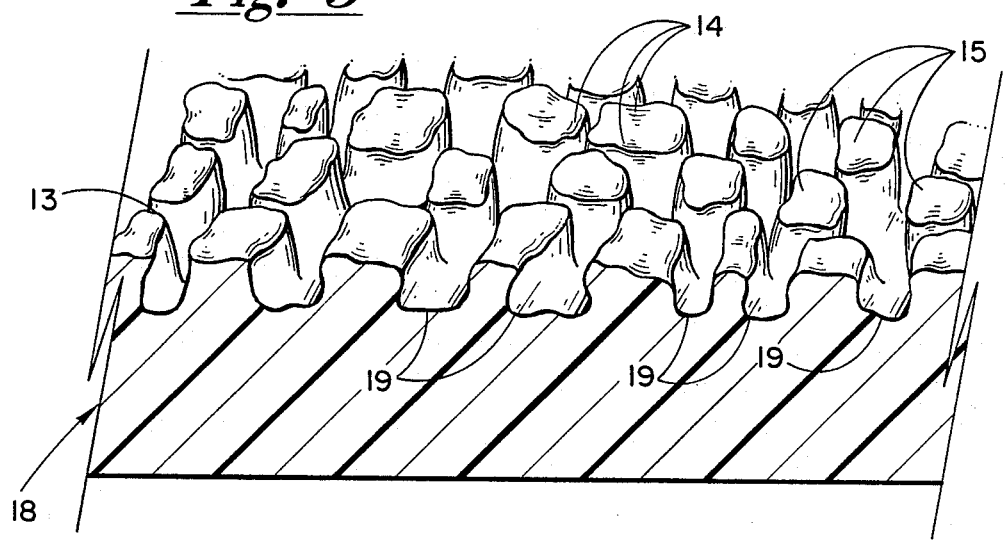
FIG. 3 is a perspective view of a cut-away portion of the silicone rubber film utilized in the device shown in FIG. 1, with FIG. 3 being shown on a substantially enlarged scale.

In accordance with the structure illustrated in the drawings, and with particular attention being directed to FIGS. 1 and 2, the breast prosthesis device generally designated 10 includes a shell or layer of silicone rubber 11 surrounding and forming a three-dimensional cavity as shown at 12. The surface of layer 11 is textured so as to form a net-like surface grid structure including pillars extending outwardly from a base plane as shown at 13, along with indentations or pores being formed in the outer end projecting surfaces of pillars 13 as at 14 (FIG. 3). In other words, the outer ends 15 of the individual pillars, such as pillars 13—13, contain pores, such as pores 14, formed therein.

With continued attention being directed to FIGS. 2 and 3 of the drawings, a mold having a surface arranged as the reverse image of the desired textured structure is formed so as to create the desired surface configuration of the silicone rubber layer shown generally at 18. Projections are formed in the mold so as to create valleys in the finished product, such as valleys 19—19 as illustrated in FIG. 3. As indicated hereinabove, the creation of the textured surface including the pillars 13—13 has been found to promote tissue ingrowth and thus improve the quality of the soft, pliable three-dimensional prosthesis means of the present invention.

Attention is now directed to the alternate preferred embodiment illustrated in FIGS. 4 and 5 of the drawings. Specifically, the soft, pliable prosthesis device means shown generally at 25 is provided with a single or double lumen filling tube as shown generally at 26, with a silicone rubber layer piercing needle 27 being coupled to the distal end of single or double lumen device 26. Fitting 28 is provided in order to secure single or double lumen device 26 to the needle 27. Tubing 29, which is illustrated as a single lumen in FIGS. 4 and 5, is shown coupled to needle 27 through fitting 28.

The exterior surface 30 of soft, pliable prosthesis 25 is textured in the same fashion as that embodiment illustrated in FIGS. 1–3. This surface includes, as indicated, valleys as at 32, and irregular end surfaces 33 of individual pillar structures. The extreme outer ends 34 of the individual pillars is also illustrated.

A gel solution may be employed as an inflatable or filling material for the interior core of the silicone rubber device, it being understood that a saline solution may be suitably employed as well.

The ultimate thickness of the silicone layer is shown generally as at 36 in FIG. 5, with the inner depths of the individual inter-pillar valleys being shown further at 37—37.

Other and further embodiments of the present invention may be obvious to those of ordinary skill in the art, with certain other embodiments reasonably falling within the scope of the claims herein.

What is claimed is:

1. In a soft, pliable three-dimensional prosthesis means for implantation in humans and comprising a three-dimensional solid with an outer layer of silicone rubber and having outer surfaces of the silicone rubber layer treated for formation of host-prosthesis interface, the improvement comprising:
   (a) interstices formed on said outer silicone rubber surfaces to produce a substantially continuous, textured surface and characterized by a net-like, three-dimensional grid structure with pores having multi-planar, random axis orientation to provide for mechanical ingrowth of host fibrous tissue into and around said surface pores and interstices;
   (b) the said net-like surface grid structure of said silicone rubber layer including substantially randomly placed formed pillars of non-uniform length and area extending outwardly from a base plane and with valleys disposed between said pillars, said pillars further having irregular outer end surfaces with indentations formed therein; and
   (c) said pillars and indentations generally providing a textured surface which approximates a surface having average pore size ranging from between about 20 and 100 microns.

2. The soft, pliable three-dimensional prosthesis means as defined in claim 1 being particularly characterized in that said soft, pliable three-dimensional prosthesis is a breast prosthesis.

3. The soft, pliable three-dimensional prosthesis means as defined in claim 1 being particularly characterized in that said prosthesis means includes an outer layer of silicone rubber enclosing a hollow core, and wherein the hollow core is filled with liquid silicone gel.

4. The soft, pliable three-dimensional prosthesis means as defined in claim 1 being particularly characterized in that said pillars are separated by valley zones, and wherein said pillars extend outwardly between about 20 microns and 800 microns from the surface of the valleys.

5. The soft, pliable three-dimensional prosthesis means as defined in claim 4 being particularly characterized in that pores formed at the outer ends of said pillars are between about 20 microns and 800 microns in depth.

* * * * *